US006352960B1

(12) United States Patent
Teraoka et al.

(10) Patent No.: US 6,352,960 B1
(45) Date of Patent: Mar. 5, 2002

(54) CONTROLLING AGENT FOR AGRICULTURAL OR HORTICULTURAL BACTERIAL DISEASE

(75) Inventors: Takeshi Teraoka; Shigeki Tanino, both of Yokohama (JP)

(73) Assignees: Meiji Seika Kaisha, Ltd.; Dainippon Ink and Chemicals, Inc., both of Tokyo (JP)

( * ) Notice: Subject to any disclaimer, the term of this patent is extended or adjusted under 35 U.S.C. 154(b) by 0 days.

(21) Appl. No.: 09/719,287

(22) PCT Filed: Jun. 10, 1999

(86) PCT No.: PCT/JP99/03104

§ 371 Date: Dec. 11, 2000

§ 102(e) Date: Dec. 11, 2000

(87) PCT Pub. No.: WO99/63827

PCT Pub. Date: Dec. 16, 1999

(30) Foreign Application Priority Data

Jun. 12, 1998 (JP) ............................. 10-164022

(51) Int. Cl.⁷ .................. A01N 35/10; A01N 43/40; A01N 43/02; A01N 43/16; A01N 47/40; A61K 31/54; A61K 31/35
(52) U.S. Cl. ................ 504/343; 504/130; 504/140; 514/224.5; 514/460; 514/635
(58) Field of Search ................. 504/117, 130, 504/140, 343; 514/224.8, 460, 635

(56) References Cited

FOREIGN PATENT DOCUMENTS

| JP | 43-27335 | 11/1943 |
|---|---|---|
| JP | 50-105906 | 8/1975 |
| JP | 50-121435 | 9/1975 |
| JP | 53127829 | * 11/1978 |
| JP | 56-95102 | 8/1981 |
| JP | 56-99403 | 8/1981 |
| JP | 56-145205 | 11/1981 |
| JP | 57-7605 | 2/1982 |
| JP | 57-48902 | 3/1982 |
| JP | 57-61252 | 12/1982 |
| JP | 63-250306 | 10/1988 |
| JP | 2-4569 | 1/1990 |
| JP | 6-234608 | 8/1994 |
| JP | 7-5537 | 1/1995 |

OTHER PUBLICATIONS

Dekker, Agricultural use of antibiotics, 1971, World Rev. Pest Contr., vol. 10, pp. 9–23.*

Farm Chemical Handbook (1997).

The Pesticide Manual (1997, pp. 651–653 and pp. 709–712).

* cited by examiner

Primary Examiner—Alton Pryor
(74) Attorney, Agent, or Firm—Armstrong, Westerman & Hattori, LLP

(57) ABSTRACT

A controlling agent for agricultural or horticultural, which is less phytotoxic and which has considerable controlling effect against bacterial plant diseases, is provided by using bis(8-guanidinooctyl) amine or salts thereof as an active ingredient. By using, together with bis(8-guanidinooctyl) amine or salts thereof, other active ingredient of a controlling agent for agricultural or horticultural bacterial disease than these compounds, the controlling agent for agricultural or horticultural having an even higher effect is provided.

9 Claims, No Drawings

CONTROLLING AGENT FOR AGRICULTURAL OR HORTICULTURAL BACTERIAL DISEASE

This application is a 371 of PCT/JP99/03104 filed Jun. 10, 1999.

TECHNICAL FIELD

The present invention relates to a controlling agent for agricultural or horticultural bacterial disease comprising bis(8-guanidinooctyl)amine or salts thereof as an active ingredient, to a controlling agent for agricultural or horticultural bacterial disease obtained by adding to the controlling agent, other active ingredient of a controlling agent for agricultural or horticultural bacterial disease than bis(8-guanidinooctyl)amine or salts thereof, and to a method for controlling bacterial diseases in the field of agriculture and horticulture using them.

BACKGROUND ART

Bacterial plant diseases are known to be diseases difficult to control, and inorganic copper agents, organic copper agents, streptomycin agents, oxolinic acid, etc. are used as controlling agent therefor. However, sufficient controlling effects cannot always be obtained depending on the crop. Some combinations of agents and crops may be impossible to use due to phytotoxicity. Therefore, development of controlling agents having a novel effect is keenly desired.

There has been found no drug having controlling effects on both plant diseases caused by fungi (filamentous fungi) and bacterial plant diseases except copper agents. To control both of them simultaneously, it has been necessary to use a plurality of different components in admixture.

Bis(8-guanidinooctyl)amine has another name of Iminoctadine. Salts thereof, Iminoctadine acetic acid salt and Iminoctadine arbesylic acid salt (hereinafter, abbreviated as "Iminoctadine ABS salt") have broad anti filmentaus fungi spectra and are utilized as controlling agent for agricultural or horticultural disease not only in our country but also overseas. However, for bacterial diseases, the effect of these compounds has not been known presumably due to the fact that they exhibit almost no antibacterial activity in vitro. Consequently no case has been known at all in which they are used as controlling agent for bacterial plant disease.

The first patent application in reference to Iminoctadine is Japanese Patent Publication (Kokoku) No. Sho 43-27335, which discloses that guanidino derivatives including Iminoctadine are also effective against pathogenic bacteria. However, though it is described that, in the test example, bis (10-guanidinodecyl) amine sulfate and bis (12-guanidinododecyl) amine hydrochloride revealed to have in vitro antibacterial activity against plant pathogenic bacteria such as the genus Xanthomonas and the genus Pseudomonas but bis (8-guanidiooctyl) amine sulfate has no activity thereagainst.

Later on, many related patent applications (Japanese Patent Laid-open (Kokai) No. Sho 50-105906, Japanese Patent Laid-open (Kokai) No. Sho 56-95102, Japanese Patent Laid-open (Kokai) No. Sho 57-48902, Japanese Patent Publication (Kokoku) No. Sho 57-61252, Japanese Patent Publication (Kokoku) No. Sho 57-7605, Japanese Patent Publication (Kokoku) No. Hei 2-4569, Japanese Patent Publication (Kokoku) No. Hei 7-5537, Japanese Patent Laid-open (Kokai) No. Hei 6-234608) have been filed. However, no mention has been made of therein that Iminoctadine and salts thereof are effective in controlling bacterial plant diseases.

In Japan, Iminoctadine acetic acid salt and Iminoctadine ABS salt have not been recorded in agricultural chemicals register as controlling agent for bacterial plant disease. There is no description that the aforementioned agents have controlling effects on bacterial plant diseases, in technical informations or literature on the agent. Compounds such as Guazatine, Befran (Iminoctadine acetic acid salt) and Bellkute (Iminoctadine ABS salt) were described in Farm Chemicals Handbook (1997) and Guazatine and Iminoctadine were described in Pesticide Manual (1997 p.651–653, p.709–710). However, in neither case there is a description that these compounds are effective against bacteria.

As a reason that it is difficult to develop controlling agents for bacterial plant disease, it is well known that there are many cases where substances which exhibit extremely high antibacterial activity in vitro cannot be expected to exhibit sufficient effects in the field. Conversely, no agent has been known that has no activity in vitro but exhibits high effect in vivo.

As for the agents currently used as controlling agent for bacterial plant disease, few controlling agents exhibit sufficient effects due to insufficiency of absorption and transition or residual activity so is that bacterial plant diseases have been regarded as the difficult-to-control diseases. Use of mixed preparations and in situ mixing and spreading by cultivators have taken place frequently and stronger controlling agents are desired.

To decrease the incidence of drug resistant bacteria and prevent the proliferation of drug resistant bacteria, development of novel controlling agent for bacterial plant disease, which has different effect, is keenly desired.

That is, it has been known that copper preparations have sterilization effect due to release of copper ions, oxolinic acid causes inhibition of replication of DNA, and streptomycin agents cause translation error and coupling inhibition of mRNA, and development of agents which show difference in effect from any of them has been desired.

SUMMARY OF THE INVENTION

The present inventors made extensive research on agents which have less phytotoxicity and which are effective against bacterial plant diseases known as difficult-to-control diseases and, as a result, have found that Iminoctadine and salts thereof exhibit considerable controlling effects on bacterial plant diseases, thus achieving the present invention.

Further, the present inventors have found that the addition of inorganic copper agents, organic copper agents, streptomycin agents, oxolinic acid, kasugamycin or the like, which have been used as controlling agent for agricultural or horticultural bacterial disease in the past, to Iminoctadine increases the controlling effects, thus achieving the present invention.

In addition, since the mixed agent contains Iminoctadine having a new effect, it is expected that the mixed agent will defer and suppress emergence of drug resistant bacteria.

The present inventors have made extensive research with a view to solving these problems and have conducted field tests using Iminoctadine or salts thereof, which have hitherto been known to be effective against filamentous fungi but have not been known as controlling agent for bacterial disease, solely or in combination with other active ingredient of a controlling agent for agricultural or horticultural bacterial disease than Iminoctadine. As a result, the present inventors have found, surprisingly, that Iminoctadine alone exhibited high controlling effect, and that mixed agent containing Iminoctadine and the other active ingredient of controlling agent for agricultural or horticultural bacterial disease than Iminoctadine exhibited extremely high controlling effect due to synergistic effect.

That is, the present invention relates to a controlling agent for agricultural or horticultural bacterial disease containing Iminoctadine or salt thereof.

The present invention also relates to a mixed agent containing the above controlling agent and the other active ingredient of controlling agent for agricultural or horticultural bacterial disease than Iminoctadine or salt thereof.

The present invention further relates to a method for controlling bacterial diseases in the field of agriculture and horticulture, which comprises the step of applying the controlling agent for agricultural or horticultural bacterial disease containing Iminoctadine or salt thereof, or a mixed agent prepared by adding the other active ingredient of controlling agent for agricultural or horticultural bacterial disease than Iminoctadine or salt thereof to the controlling agent, to a crop or to a field.

In this specification,

"Controlling agent for agricultural or horticultural disease" refers to a agent which suppress proliferation of pathogenic microbe that have infected agricultural or horticultural crops and which control various damages caused by diseases. "Controlling agent for agricultural or horticultural bacterial disease" refers to the agent in the case where the pathogenic microbe is a bacterium.

"Plant disease" refers to a disease of plant caused by the infection of pathogenic microbes such as fungi or bacteria. "Bacterial plant disease" refers to the disease of plant in the case where the pathogenic microbe is a bacterium.

Hereinafter, the present invention will be described in detail.

Iminoctadine acetic acid salt and Iminoctadine ABS salt have broad anti filamentous fungi spectra and are utilized as controlling agent for agricultural or horticultural disease not only in our country but also overseas.

However, as described above, Iminoctadine have been used only as controlling agent for plant diseases caused by filamentous fungi, and their effect as controlling agent for bacterial disease has not been known or no case has been known at all in which they are used as controlling agent for bacterial plant disease.

Iminoctadine or salts thereof when mixed with other controlling agent for agricultural or horticultural bacterial disease such as inorganic copper agents, organic copper agents, streptomycin agents, oxolinic acid, and kasugamycin increase the controlling effects of the agents against the bacterial plant diseases, so that a controlling agent for disease, which defer and suppress the development of resistant bacteria to both agents can be provided by mixing them.

The compound of the present invention, Iminoctadine, is an amine and therefore it virtually exists as a base so that agriculturally or horticulturally acceptable salts can be formed by reacting it with many inorganic or organic acids. That is, the salts can be formed using hydrochloric acid, nitric acid, sulfuric acid, hydrobromic acid, hydroiodic acid, phosphorous acid or the like. Similarly, there can be formed salts derived from nontoxic organic acids such as aliphatic monocarboxylic acids and aliphatic dicarboxylic acids, amino acids, phenyl-substituted alkanoic acids, hydroxyalkanoic acids, hydroxyalkanedioic acids, aromatic acids, and aliphatic sulfonic acids and aromatic sulfonic acids.

In this specification, "salts" refers to agriculturally or horticulturally acceptable salts as described above and specifically include hydrochloric acid salts, nitrate, sulfate, pyrosulfate, bisulfate, sulfite, bisulfite, phosphate, hydrogen phosphate, dihydrogen phosphate, metaphosphate, pyrophosphate, chloride, bromide, iodide, acetate, propionate, caprylate, acrylate, formate, tartarate, isobutyrate, caprate, heptanate, propiolate, oxalate, malonate, succinate, suberate, sebacate, fumarate, maleate, mandelate, butyne-1,4-dioic acid salts, hexyne-1,6-dioic acid salts, hippurate, benzoate, chlorobenzoate, methylbenzoate, phthalate, terephthalate, benzenesulfonate, toluenesulfonate, chlorobenzenesulfonate, dodecylbenzenesulfonate, xylenesulfonate, phenylsulfonate, phenyl acetate, phenylpropionate, phenylbutyrate, citrate, lactate, β-hydroxybutyrate, glycolate, malate, naphthalene-1-sulfonate, naphthalene-2-sulfonate, methanesulfonate, etc.

The controlling agent for agricultural or horticultural bacterial disease of the present invention contains Iminoctadine or salts thereof as described above. "Iminoctadine or salts thereof" does not mean that they are always selected alternatively but it may be one of Iminoctadine or salts thereof or it may include both of them. The salt of Iminoctadine may also be one or a mixture including two or more.

The other controlling agent for agricultural or horticultural bacterial disease than Iminoctadine or salts thereof includes inorganic copper agents; organic copper agents; streptomycin agents such as streptomycin sulfate; oxolinic acid; kasugamycin agents such as kasugamycin hydrochloric acid salt; tetracycline agents; etc., but it is not limited thereto as far as it does not impair the controlling effect of Iminoctadine or salts thereof on the bacterial plant diseases.

In the practice of the present invention, where the occurrence of bacterial plant diseases is anticipated, applying an aqueous solution of the controlling agent for agricultural or horticultural bacterial disease of the present invention to the field or to crops par advance by spreading or by various methods which can be adopted in agricultural operations such as administering and immersing, can preventively control the occurrence of bacterial plant diseases. Alternatively, the object of controlling the diseases by applying the agent after the occurrence of bacterial plant diseases to suppress the occurrence of diseases or proliferation thereof.

The dose of the controlling agent for agricultural or horticultural bacterial disease of the present invention may vary appropriately depending on the form of preparation, or the method to be used, object or time of application. Usually, it is desirable to use the agent in an amount of 50 to 5,000 g per hectare (ha) as the amount of Iminoctadine, which is the active ingredient.

In the mixed agent of Iminoctadine or salts thereof and the other controlling agent for agricultural or horticultural bacterial disease than Iminoctadine or salts thereof, it is preferred that the mixing ratio by weight be in the range of 0.001 to 1,000 fold, preferably 0.01 to 100 fold, and more preferably 0.1 to 10 fold.

In the practice of the present invention, Iminoctadine or salts thereof, or Iminoctadine or salts thereof and the other active ingredient of controlling agent for agricultural or horticultural bacterial disease than Iminoctadine or its salts, may be used as they are. In practice, various carriers may be used and, if necessary, suitable adjuvants may be further blended. Then all ingredients may be pharmaceutical manufactured into preparation forms that are usually applied to controlling agents for agricultural or horticultural disease, for example, oil solution, emulsion, dusting powder, solution, wettable powder, granule, suspension, etc., which may be suitably diluted before use.

The carriers which can be used include solid powder or granular carriers such as clay, talc, diatomaceous earth, terra alba, calcium carbonate, silicic anhydride, bentonite, sodium sulfate, silica gel, organic acid salts, sugars, starch, resins, synthetic or natural polymers; and liquid carriers, for examples, aromatic hydrocarbons such as xylene, aliphatic hydrocarbons such as kerosene, ketones such as methyl ethyl ketone, cyclohexanone and isophorone, lactams, ethers such as anisole, alcohols such as ethanol, propanol and ethylene glycol, esters such as ethyl acetate and butyl acetate, dimethyl sulfoxide, dimethylformamide, water, etc.

Further, to secure the effect of pharmaceutical manufacturing, it is desirable to use adjuvants such as emulsifiers, dispersants, humectants, binders, glues, and lubricants by suitably selecting or combining them so as to meet the purpose. Examples of such adjuvants include nonionic or ionic surfactants, carboxymethylcellulose, polyvinyl acetate, gums, calcium stearate, wax, etc.

In the controlling agent for agricultural or horticultural bacterial disease of the present invention, it is desirable that Iminoctadine or the other active ingredient of controlling agent for agricultural or horticultural bacterial disease than Iminoctadine may be contained usually in an amount of 0.01 to 10% in the case of dusting powder, 1 to 90% in the case of wettable powder, 0.01 to 20% in the case of granule, 1 to 60% in the case of solution, and 5 to 80% in the case of suspension.

In using the controlling agent for agricultural or horticultural bacterial disease of the present invention, it may of course be used alone. It is also possible to use the controlling agent together with agricultural chemicals such as fungicides, insecticides, herbicides, and plant growth regulators; fertilizers; or soil amendments; etc. or to use in the form of mixed agent therewith.

The present invention is not particularly limited but the controlling agent of the present invention is effective in controlling the diseases that are caused by plant pathogenic bacteria belonging to the following genera:

Erwinia, Pseudomonas,

Xanthomonas, Corynebacterium,

Agrobacterium, Streptomyces

Of those, the controlling agent of the present invention is effective especially for the diseases caused by bacteria belonging to the genera Erwinia, Pseudomonas, and Xanthomonas.

Though not particularly limited, the controlling agent of the present invention can be used for controlling various bacterial diseases occurring in agriculture or horticulture cultivation including specialties crops such as craft crops, oil and fat crops, and fiber crops; lawn; and grass.

For example, citrus canker, apple fire blight, pear fire blight, peach bacterial short hole, apricot bacterial short hole, Japanese apricot bacterial canker, prune black spot, prune bacterial canker, Cucurbitaceae bacterial spot, brassicaceous vegetables' black rot, brassicaceous vegetables' bacterial black spot, vegetables' soft rot, lettuce bacterial rot, konyaku (Amorphophalus Konjac K. Koch) soft rot, tobacco wildfire, tobacco angular leaf spot, mulberry bacterial blight, rice bacterial leaf blight, rice bacterial grain rot, kiwii fruit bacterial blossom blight, potato scab, tomato bacterial wilt, peach/prune crown gall, etc.

For controlling in a leaf developing stage of stone fruits such as Japanese apricot and peach, copper agents cannot be used in mixed preparations because of phytotoxicity of copper. Therefore the range of selection has been narrowed extremely. However, mixed use of, for example, streptomycin agent and Iminoctadine ABS salt can considerably increase the controlling effect.

The target crops in the present invention are not particularly limited and include cereals (wheat, barley, rye, aits, rice plant, sorghum, related crops, etc.), beat, pear-like fruits, stone fruits, and soft fruits (apple, pear, plum, peach, Japanese apricot, prune, almond, cherry, strawberry, raspberry, and black berry, etc.), legumes (kidney bean, lentil, pea, soy bean), oil plants (rape, mustard, poppy, olive, sunflower, coconut, castor-oil plant, cocoa bean, peanut, etc.), Cucurbitaceae (pumpkin, cucumber, melon, etc.), fiber plants (cotton, flax, hemp, jute, etc.), citrus (orange, lemon, grape fruit, mandarin, Watson pomelo (citrus natsudaidai), etc.), vegetables (lettuce, cabbage, celery cabbage, Chinese radish, carrot, onion, tomato, potato, green pepper, etc.), camphor trees (avocado, cinnamon, camphor, etc.), corn, tobacco, nuts, coffee, sugar cane, tea, grapevine, hop, banana, and plants such as natural rubber plant, as well as ornamental plants (flower, bushes, broad-leaf trees and evergreen trees), etc.

BEST MODE FOR CARRYING OUT THE INVENTION

Hereinafter, examples of the present invention will be shown. However, the present invention should not be limited thereto.

PREPARATION EXAMPLE 1

12.5 Parts by weight of streptomycin sulfate (Meiji Seika Kaisya, Ltd.), 20 parts by weight of Iminoctadine ABS salt (Dainippon Ink and Chemicals, Inc.), 27.5 parts by weight of white carbon, 35 parts by weight of diatomaceous earth, and 5 parts by weight of polyoxyethylene alkyl aryl ether were mixed to obtain wettable powder.

PREPARATION EXAMPLE 2

25 Parts by weight of streptomycin sulfate, 40 parts by weight of Iminoctadine ABS salt, 30 parts by weight of white carbon, and 5 parts by weight of polyoxyethylene alkyl aryl ether were mixed to obtain wettable powder.

PREPARATION EXAMPLE 3

20 Parts by weight of oxolinic acid, 40 parts by weight of Iminoctadine ABS salt, 35 parts by weight of white carbon, and 5 parts by weight of polyoxyethylene alkyl aryl ether were mixed to obtain wettable powder.

PREPARATION EXAMPLE 4

5 Parts by weight of kasugamycin hydrochloric acid salt, 60 parts by weight of basic copper chloride, 10 parts by weight of Iminoctadine ABS salt, 20 parts by weight of white carbon, and 5 parts by weight of polyoxyethylene alkyl aryl ether were mixed to obtain wettable powder.

Next, following test examples show that the controlling agent of the present invention has superior controlling effect against bacterial plant disease.

The preventive values or expected preventive values used in the test examples in this specification were all calculated using the following equations.

Preventive value=(1−disease severity of treated lot/disease severity of non-treated lot)×100

(Disease severity may be replaced by degree of damage or ratio of damage.)

(Colby's calculation equation)

$$E=(X+Y)-X\times Y\div 100$$

X: Preventive value in case of using the active ingredient compound A at the concentration of m ppm;

Y; Preventive value in case of using the active ingredient compound B at the concentration of n ppm;

E: Expected preventive value (hereinafter, referred to as "expected preventive value") in case of using the active ingredient compound A at the concentration of m ppm and the active ingredient compound B at the concentration of n ppm.

Generally, if the preventive value obtained by actually mixing and using the compounds is greater than the expected preventive value, it can be said that there exhibits synergism in that combination.

Test Example 1 in vitro Antibacterial Tests on Various Plant Pathogenic Bacteria Each agent was dissolved in sterilized water and added to PDA culture medium (Nissui Seiyaku Co., Ltd.) and Japanese apricot canker bacterium (*Pseudomonas syringae* pv. *morsprunorum*), vegetables' soft rot disease bacterium (*Erwinia carotovora* sub-sp. *cartovora*), and citrus canker bacterium (*Xanthomonas campestris* pv. *citri*) were inoculated.

The Japanese apricot canker bacterium was cultivated at 21° C., the vegetables' soft rot disease bacterium and citrus canker bacterium were cultivated at 28° C. After 3 days from the start of cultivation, the growth of bacteria was monitored. The results are shown in Table 1.

TABLE 1 in vitro Antibacterial Tests on Various Pathogenic Bacteria

|  |  | Pseudomonas syringae pv. morsprunorum | Erwinia carotovora sub-sp. Carotovora | Xanthomonas campestris pv. citri |
|---|---|---|---|---|
| Non-treated lot |  | +++ | +++ | +++ |
| Iminoctadine | 1 ppm | +++ | +++ | +++ |
| ABS salt | 10 ppm | +++ | +++ | +++ |
|  | 100 ppm | ++ | +++ | +++ |
| Streptomycin | 1 ppm | ++ | + | ++ |
| sulfate | 10 ppm | + | − | + |
|  | 100 ppm | − | − | − |
| Oxolinic | 1 ppm | ++ | − | +++ |
| acid | 10 ppm | − | − | ++ |

+++: Colonies grew well;
++: Growth was slightly suppressed;
+: Growth was strongly suppressed but proliferation was observed; and
−: No proliferation was observed.

As shown in Table 1, Iminoctadine ABS salt under the in vitro conditions did not suppress the growth of Japanese apricot canker bacterium (*Pseudomonas syringae* pv. *morsprunorum*), vegetables' soft rot disease bacterium (*Erwinia carotovora* sub-sp. *cartovora*), and citrus canker bacterium (*Xanthomonas campestris* pv. *citri*) even added at the concentration of 100 ppm.

Test Example 2 Controlling Effect on Japanese Apricot Bacterial Canker (1)

Commercially available Agrepto wettable powder containing 25% of streptomycin sulfate (20% as streptomycin) or commercially available Iminoctadine ABS salt [trade name: Bellkute wettable powder (40%)] was diluted to a predetermined concentration and tested. Also, the preparation produced according to Preparation Example 2 was diluted to a predetermined concentration and tested.

Young 5-year old Japanese apricot trees which frequently suffered from Japanese apricot bacterial canker in the preceding year, were tested. Predetermined agents were continually sprayed four times with intervals of 10 days starting from early April. In May, the disease severity of Japanese apricot bacterial canker was searched on 100 fruits per tree for total 5 trees in each lot and the results were evaluated by 5-rank indices.

The damaged fruits were searched and disease severity and preventive value were calculated using the indices and equation below. The results are shown in Table 2.

(Indices)
0: None=No lesion
1: Few=1 to 5 lesions
2: Medium=6 to 15 lesions
4: Many=16 to 30 lesions
6: Extreme=31 or more lesions or with cracks Disease severity=$\Sigma$(Index×The number of damaged fruits per degree)÷(6×The number of tested fruits)×100

TABLE 2

Controlling Effect on Japanese Apricot Bacterial Canker

|  | The number of damaged fruits | Disease severity | Preventive value | Expected preventive value |
|---|---|---|---|---|
| Non-treated lot | 31 | 3.7 | 0 |  |
| Iminoctadine 200 ppm ABS salt | 18 | 1.2 | 68 |  |
| Streptomycin 125 ppm Sulfate | 23 | 1.6 | 57 |  |
| 2000-fold solution of Preparation Example 2 |  |  |  |  |
| Iminoctadine 200 ppm ABS salt Streptomycin 125 ppm sulfate | 7 | 0.4 | 90 | 86 |

Test Example 3 Controlling Effect on Japanese Apricot Bacterial Canker (2)

Japanese apricot seedlings rested for the winter season in the open field were cut to the height of 60 cm and transplanted to 1/5000 a Wagner pots and allowed to sprout and develop leaves in a greenhouse were tested. After giving fine bruises to the leaves with Carborandum, water was sprayed sufficiently to flow away the Carborandum. After air drying, the agents diluted to predetermined concentrations with water were sprayed onto the leaves, which were air dried again. Japanese apricot canker bacterium (*Pseudomonas syringae* pv. *morsprunorum*) preliminarily cultivated in PPG medium (200 g of potato, 3 g of disodium phosphate (dodecahydrate), 0.5 g of dikalium phosphate, 5 g of peptone, 3 g of sodium chloride, 5 g of glucose, 1 L of distilled water) was inoculated by spraying together with the medium. The inoculated plants were placed under controlled humid conditions (temperature 20° C., humidity 99% to 100%) for 40 hours and then transferred to a greenhouse to allow the disease to emerge. After 7 days, the lesion area in each lot was measured and disease severity and preventive value were calculated according to the following indices. The results are shown in Table 3.

(Indices)

0: No lesion;

1: Several lesions on the leaves of one branch;

2: The damaged area was less than ¼ of the total area of the leaves on one branch;

3: The damaged area was from ¼ to less than ½ of the total area of the leaves on one branch;

4: The damaged area was from ½ to less than ⅔ of the total area of the leaves on one branch; and 5: The damaged area was ⅔ or more of the total area of the leaves on one branch.

Disease severity=Σ(Index×The number of data)÷(Total number of data×5)×100

TABLE 3

Controlling Effect on Japanese Apricot Bacterial Canker

|  |  | Disease severity | Preventive value | Expected preventive value |
|---|---|---|---|---|
| Non-treated lot |  | 71 | 0 |  |
| Iminoctadine ABS salt | 200 ppm | 19 | 73 |  |
| Streptomycin sulfuric acid salt | 125 ppm | 24 | 67 |  |
| 1000-fold solution of Preparation Example 1 |  |  |  |  |
| Iminoctadine ABS salt | 200 ppm | 6 | 92 | 91 |
| Streptomycin sulfate | 125 ppm |  |  |  |

Test Example 4 Controlling Effect on Citrus Canker

Commercially available Agrepto wettable powder containing 25% of streptomycin sulfate (20% as streptomycin) or commercially available Iminoctadine ABS salt [trade name: Bellkute wettable powder (40%)] was diluted to a predetermined concentration and tested. The preparations produced according to Preparation Examples 2 and 4 were also diluted to predetermined concentrations. 20 new leaves of pot-grown Watson pomelo were tested for each of the preparations. After wounding the leaves with a needle, each predetermined agent solution was sprayed thereon and the leaves were air dried. Then, citrus canker bacterium (*Xanthomonas campestris* pv. *citri*) was inoculated with the density of 1×10⁶ cells. Thereafter, the trees were put into controlled cultivation in a greenhouse. After 1 month, the emergence of citrus canker was investigated. The results are shown in Table 4.

TABLE 4

Controlling Effect on Citrus Canker Bacterial Canker

|  |  | The number of suffering leaves | Ratio of suffering leaves | Preventive value | Expected preventive value |
|---|---|---|---|---|---|
| Non-treated lot |  | 20 | 100 | 0 |  |
| Iminoctadine ABS Salt | 400 ppm | 3 | 15 | 85 |  |
|  | 100 ppm | 5 | 25 | 75 |  |
|  | 50 ppm | 9 | 45 | 55 |  |
| Streptomycin Sulfate | 500 ppm | 1 | 5 | 95 |  |
|  | 125 ppm | 4 | 20 | 80 |  |
|  | 62.5 ppm | 8 | 40 | 60 |  |

TABLE 4-continued

Controlling Effect on Citrus Canker Bacterial Canker

|  |  | The number of suffering leaves | Ratio of suffering leaves | Preventive value | Expected preventive value |
|---|---|---|---|---|---|
| Kasugamycin hydrochloric acid salt | 50 ppm | 5 | 25 | 75 |  |
| Basic copper chloride | 600 ppm |  |  |  |  |
| 4000-fold solution of Preparation Example 2 |  |  |  |  |  |
| Iminoctadine ABS salt | 100 ppm | 0 | 0 | 100 | 90 |
| Streptomycin Sulfate | 62.5 ppm |  |  |  |  |
| 1000-fold solution of Preparation Example 4 |  |  |  |  |  |
| Iminoctadine ABS salt | 100 ppm | 7 | 5 | 95 | 94 |
| Kasugamycin hydrochloric acid salt | 50 ppm |  |  |  |  |
| Basic copper chloride | 600 ppm |  |  |  |  |

Test Example 5 Controlling Effect on Celery Cabbage Soft Rot

Commercially available Agrepto wettable powder containing 25% of streptomycin sulfate (20% as streptomycin) or commercially available Iminoctadine ABS salt [trade name: Bellkute wettable powder (40%)] was diluted to a predetermined concentration and tested. The preparations produced according to Preparation Examples 1 and 3 were also diluted to predetermined concentrations. In early August, Celery cabbages were sown in 5.2 m² per lot in triplicate. From 20 September when the plant reached 10-leaf stage, the predetermined agents were continually sprayed 3 times with intervals of 7 days. In late October, the disease severity and degree of damage of Celery cabbage soft rot were investigated using 4-rank indices. The results obtained are shown in Table 5.

(Indices)

0: No damage;

1: Only a portion of outer leaves damaged;

2: A portion of outer leaves and head portion damaged; and

3: Most part of head portion damaged.

Degree of damage=Σ(Index×the number of individuals)÷(the number of individuals searched×3)×100

TABLE 5

Controlling Effect on Celery Cabbage Soft Rot

|  |  | The number of individuals damaged | Degree of damage | Preventive value | Expected preventive value |
|---|---|---|---|---|---|
| Non-treated lot |  | 37 | 22.2 | 0 |  |
| Iminoctadine | 200 ppm | 12 | 6.4 | 71 |  |

TABLE 5-continued

Controlling Effect on Celery Cabbage Soft Rot

| | | The number of individuals damaged | Degree of damage | Preventive value | Expected preventive value |
|---|---|---|---|---|---|
| ABS salt Streptomycin sulfuric acid salt | 125 ppm | 10 | 4.6 | 79 | |
| Oxolinic acid 1000-fold solution of Preparation Example 1 | 100 ppm | 4 | 3.3 | 85 | |
| Iminoctadine ABS salt Streptomycin Sulfate 2000-fold solution of Preparation Example 3 | 200 ppm 125 ppm | 4 | 1.3 | 94 | 94 |
| Iminoctadine ABS salt Oxolinic acid | 200 ppm 100 ppm | 2 | 0.7 | 97 | 96 |

Industrial Applicability

As stated above, the present invention is to provide a novel controlling agent for agricultural or horticultural bacterial disease, which has a new effect properties. Its direct effect is to increase the certainty of bacterial disease control to stabilize yield or to broaden the width of selection of controlling agents for bacterial disease as well as to provide a method and composition for controlling, which are excellent and have not been conventionally obtained by mixing with an active ingredient of existing controlling agent for agricultural or horticultural bacterial disease.

Further, since the compounds of the present invention has totally new effect properties, it is the outstanding feature of the present invention that use of drugs having different effects in admixture can decrease the incidence of drug resistant bacteria.

What is claimed is:

1. A controlling agent for agricultural or horticultural bacterial disease comprising:
   bis(8-guanidinooctyl) amine or salts thereof as a first active ingredient; and
   streptomycin as a second active ingredient.

2. A controlling agent for agricultural or horticultural bacterial disease comprising:
   bis(8-guanidinooctyl)amine or salts thereof as a first active ingredient; and
   oxolinic acid as a second active ingredient.

3. A controlling agent for agricultural or horticultural bacterial disease comprising:
   bis(8-guanidinooctyl) amine or salts thereof as a first active ingredient; and
   kasugamycin as a second active ingredient.

4. A method for controlling bacterial diseases in the field of agriculture and horticulture, which comprises the step of applying a controlling agent for agricultural or horticultural bacterial disease, the controlling agent comprising bis(8-guanidinooctyl) amine or salts thereof as an active ingredient to a crop or to a field affected by a bacterial disease caused by a bacterium.

5. The method for controlling bacterial disease according to claim 4, wherein the bacterium is selected from the group consisting of bacterial belonging to the genera Erwinia, Pseudomonas and Xanthomonas.

6. The method for controlling bacterial disease according to claim 4 or 5, wherein the controlling agent for agricultural or horticultural bacterial disease further comprises another active ingredient of a controlling agent for agricultural or horticultural bacterial disease than bis (8-guanidinooctyl) amine or salt thereof, in addition to bis (8-guanidinooctyl) amine or salts thereof.

7. The method for controlling bacterial disease according to claim 6, wherein the other active ingredient of controlling agent for agricultural or horticultural bacterial disease than bis (8-guanidinooctyl) amine or salts thereof is streptomycin.

8. The method for controlling bacterial disease according to claim 6, wherein the other active ingredient of controlling agent for agricultural or horticultural bacterial disease than bis (8-guanidinooctyl) amine or salts thereof is oxolinic acid.

9. The method for controlling bacterial disease according to claim 6, wherein the other active ingredient of controlling agent for agricultural or horticultural bacterial disease than bis (8-guanidinooctyl) amine or salts thereof is kasugamycin.

* * * * *